(12) United States Patent
Cao

(10) Patent No.: US 9,295,537 B2
(45) Date of Patent: Mar. 29, 2016

(54) THREE DIMENSIONAL CURING LIGHT

(75) Inventor: Densen Cao, Sandy, UT (US)

(73) Assignee: CAO Group, Inc., West Jordan, UT (US)

( * ) Notice: Subject to any disclaimer, the term of this patent is extended or adjusted under 35 U.S.C. 154(b) by 0 days.

(21) Appl. No.: 12/776,695

(22) Filed: May 10, 2010

(65) Prior Publication Data

US 2010/0216089 A1 Aug. 26, 2010

Related U.S. Application Data

(63) Continuation of application No. 11/445,498, filed on Jun. 1, 2006, now abandoned.

(51) Int. Cl.
*A61C 13/15* (2006.01)

(52) U.S. Cl.
CPC ................... *A61C 19/003* (2013.01)

(58) Field of Classification Search
CPC .... A61C 19/003; A61C 19/004; A61C 1/088; A61C 9/0006; A61C 19/00; A61B 5/0088
USPC ........................ 433/29, 37, 40, 229
See application file for complete search history.

(56) References Cited

U.S. PATENT DOCUMENTS

| | | | | |
|---|---|---|---|---|
| 4,468,197 A | * | 8/1984 | Provost | 433/30 |
| 4,790,752 A | * | 12/1988 | Cheslak | 433/37 |
| 4,852,549 A | * | 8/1989 | Mori | 607/92 |
| 4,867,682 A | * | 9/1989 | Hammesfahr et al. | 433/37 |
| 5,316,473 A | * | 5/1994 | Hare | 433/29 |
| 5,487,662 A | * | 1/1996 | Kipke et al. | 433/37 |
| 5,702,250 A | * | 12/1997 | Kipke | 433/37 |
| 5,718,577 A | * | 2/1998 | Oxman et al. | 433/37 |
| 6,077,073 A | * | 6/2000 | Jacob | 433/29 |
| 6,299,441 B1 | * | 10/2001 | Novak | 433/29 |
| 6,368,109 B2 | * | 4/2002 | Lindquist | 433/215 |
| 6,391,283 B1 | * | 5/2002 | Jensen et al. | 424/49 |
| 6,741,410 B2 | * | 5/2004 | Plank et al. | 359/834 |
| 6,893,259 B1 | * | 5/2005 | Reizenson | 433/29 |
| 6,976,841 B1 | * | 12/2005 | Osterwalder | 433/29 |
| 2004/0224280 A1 | * | 11/2004 | Senn et al. | 433/29 |
| 2005/0202363 A1 | * | 9/2005 | Osterwalder | 433/29 |
| 2006/0040231 A1 | * | 2/2006 | Quan et al. | 433/29 |
| 2008/0032252 A1 | * | 2/2008 | Hayman et al. | 433/29 |

* cited by examiner

*Primary Examiner* — Cris L Rodriguez
*Assistant Examiner* — Hao D Mai
(74) *Attorney, Agent, or Firm* — CAO Group, Inc.

(57) ABSTRACT

A 3-dimensional curing light that can cure a light curable material, such as a dental restoration, from 3 directions at once.

11 Claims, 3 Drawing Sheets

THREE DIMENSIONAL CURING LIGHT

CROSS-REFERENCE TO RELATED APPLICATIONS

This patent application claims benefit of and priority to U.S. Provisional Patent Application Ser. No. 60/686,261 filed on Jun. 1, 2005.

TECHNICAL FIELD OF THE INVENTION

The present invention relates to the field of curing lights and, more particularly, to the field of three-dimensional curing lights.

BACKGROUND OF THE INVENTION

Although teeth have a 3-dimensional shape, prior art dental curing lights all emit light that can only be applied to one side of a tooth at a time. Exposing the entire tooth to light emitted by a curing light uses up valuable dentist chair time.

SUMMARY OF THE INVENTION

A 3-dimensional curing light is disclosed.

DETAILED DESCRIPTION OF THE INVENTION

Three-dimensional curing lights are disclosed that can emit light for polymerizing monomers into polymers from 3 sides of a tooth at the same time. This approach can also be used to enhance the properties of the cured dental composite, and to achieve a deeper cure.

Figure 1:
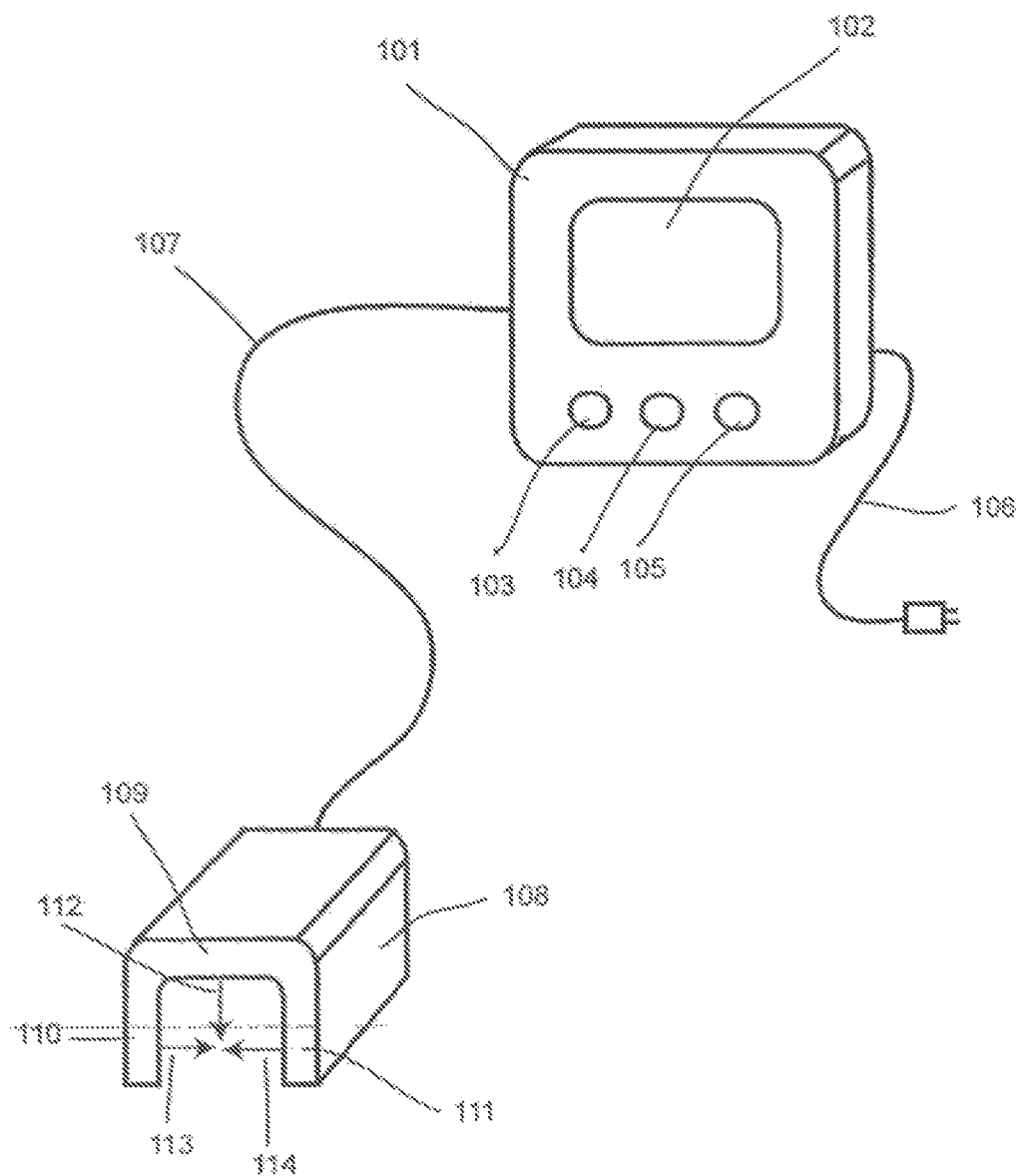
FIG. 1 depicts an example 3-dimensional curing light.

FIG. 1 depicts a perspective view of a 3-dimensional curing light. A control box 101 controls operation of the light. It includes a display 102, control buttons 103, 104, and 105 for controlling power, curing mode, and light emitting selections respectively. An electrical cord 106 is attached to the control box 101 to provide electrical power from an AC outlet. A cable 107 transfers electrical power from the control box to a 3-dimensional curing light head 108. The 3D curing light head has 3 facets, 109, 110, and 111. The 3 facets form a 3-dimensional channel. Inside the channel, the light is emitted from the inside of the facets. The light beams 112, 113, and 114 from each facet combine to cover the 3-dimensional space occupied by a tooth. Thus any three dimensional object inside the channel can be cured at once. The light emitted from the 3 facets can be controlled to be emitted together or individually depending on the need.

Figure 2:
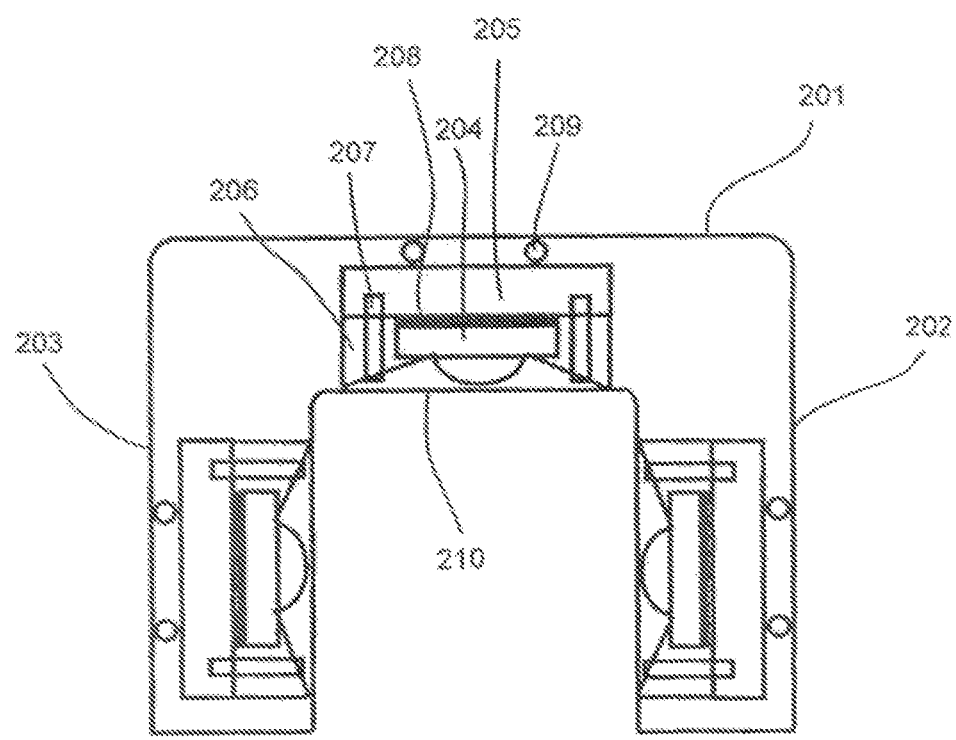
FIG. 2 depicts a cross-sectional view of an example 3-dimensional curing light.

FIG. 2 depicts a cross-sectional view of a 3-dimensional curing light head using LEDs as a light source. In the light head, there are 3 facets, 201, 202, and 203. Each facet has a similar structure and they are oriented at about 90 degrees to each other. The facets form a channel therebetween into which an object to be cured is placed. Each facet contains an LED light source 204. The LED light source can be a single LED, multiple LEDs, LED arrays, and combinations of different LEDs. The wavelength of the LEDs can range from less than 280 nm to more than 5000 nm depending on application. The power of the LEDs can range from less than 50 to more than 3000 mW/cm2. The LED light source is attached to a heat sink 205 using a fixture 206 with screw 207. There is heat conduction paste 208 located between LED 204 and heat sink 205 to facilitate heat transfer. There is a heat insulation layer 209 within the head housing to create an air gap between the heat sink and the outside casing so that the heat will not conducted to the outside casing. On the light-emitting side of the LEDs, there is a protection cover 210 to cover the LEDs and protect them from damage and contaminants. The cover 210 can be a simple protection cover, or an optical lens to shape or focus a light beam. The LED light source can contain its own heat sink so that heat sink 205 serves as a secondary heat sink for greater heat dissipation. Instead of an LED light source, a semiconductor laser or any other desired light source could be used.

Figure 3:
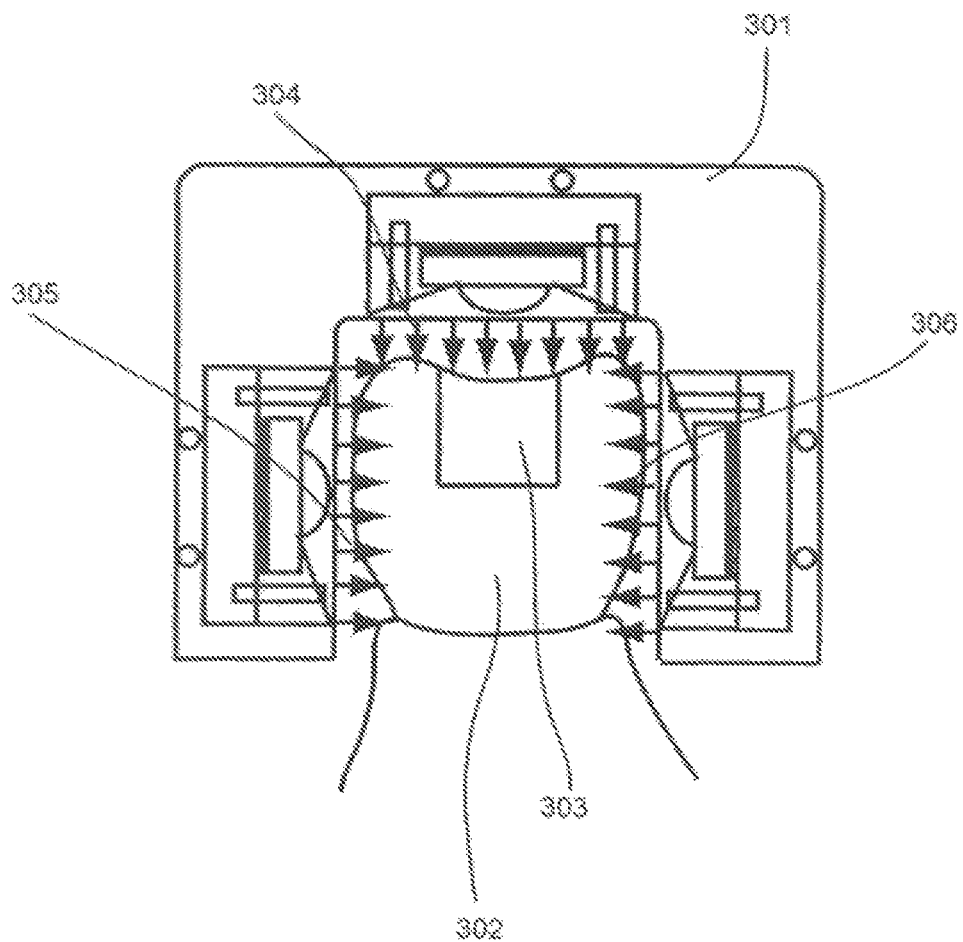
FIG. 3 depicts another cross-sectional view of an example 3-dimensional curing light.

FIG. 3 depicts the curing of a tooth filling using a 3-dimensional curing light. A light head 301 is on top of a tooth structure 302 with a filling 303 in the tooth. Three LEDs on 3 facets emit light beams 304, 305, and 306 from three sides. This allows the 3 light beams to reach the filling material from 3 directions to cure it into a durable dental restoration. Even though the light beams 305 and 306 need to penetrate the tooth structure to reach the filling material, the resulting dental restoration will be stronger and more durable than a restoration cured from one side only.

While the present invention has been described and illustrated in conjunction with a number of specific embodiments, those skilled in the art will appreciate that variations and modifications may be made without departing from the principles of the invention as herein illustrated, described, and claimed. The present invention may be embodied in other specific forms without departing from its spirit or essential characteristics. The described embodiments are to be considered in all respects as only illustrative, and not restrictive. All changes which come within the meaning and range of equivalency of the claims are to be embraced within their scope.

What is claimed is:
1. A single tooth curing light head for simultaneously emitting polymerizing light energy upon a crown and first and second exposed sides of a single tooth, comprising:
   a housing sized and configured to cover only a single tooth at a time;
   a first facet positioned within the housing, said first facet configured for facing the crown of the single tooth when the housing is placed over the single tooth;
   a second facet positioned within the housing, said second facet configured for facing the first exposed side of the single tooth when the housing is placed over the single tooth; and
   a third facet positioned within the housing, said third facet configured for facing the second exposed side of the single tooth when the housing is placed over the single tooth;
   wherein each of said first, second, and third facets, includes an outer surface and an inner surface spaced from said outer surface; wherein an LED is mounted therein each of said first, second, and third facets, within a space defined by said outer surface spaced from said inner surface; each said LED is positioned to emit light energy upon respective ones of the crown and first and second exposed sides of the single tooth; and
   wherein each LED is mounted on a heat sink, which is spaced from the respective outer surface of the first, second, and third facets, forming a heat insulation layer defined by an air gap between each said heat sink and the respective outer surface of the first, second, and third facets.

2. The curing light head of claim 1, wherein a heat conduction paste is located between each said LED and each said heat sink.

3. The curing light head of claim 1, wherein said second and third facets are oriented parallel to one another.

4. The curing light head of claim 1, wherein said first facet is oriented at about ninety degree angle with respect to at least one of the second and third facets.

5. A single tooth curing light head for emitting polymerizing light energy upon a crown and first and second exposed sides of a single tooth, comprising:
- a first facet, said first facet configured to be positioned to face the crown of the single tooth;
- a second facet, said second facet configured to be positioned to face the first exposed side of the single tooth; and
- a third facet, said third facet configured to be positioned to face the second exposed side of the single tooth;
- said first, second, and third facets combining to cover only a single tooth at one time; and
- wherein each of said first, second, and third facets, having an LED attached thereto and positioned to emit light energy upon respective ones of the crown and first and second exposed sides of the single tooth; wherein each said LED is positioned within a space defined by a corresponding outer surface and inner surface spaced from said outer surface of each of said first, second, and third facets; and
- wherein each said LED is mounted on a heat sink, which is spaced from the respective outer surface of the first, second, and third facets, forming a heat insulation layer defined by an air gap between each said heat sink and the respective outer surface of the first, second, and third facets.

6. The curing light head of claim 5, wherein said second and third facets are oriented parallel to one another.

7. The curing light head of claim 5, wherein said first facet is oriented at about ninety degree angle with respect to at least one of the second and third facets.

8. The curing light head of claim 5, wherein a heat conduction paste is located between each said LED and each said heat sink.

9. A curing light for emitting light energy upon surfaces of a single tooth, comprising:
- a first facet configured for being positioned proximate a first surface portion of the single tooth;
- a second facet configured for being positioned proximate a second surface portion of the single tooth; and
- a third facet configured for being positioned proximate a third surface portion of the single tooth; wherein
- said first, second, and third facets combining to cover only a single tooth at a time;
- wherein each of said first, second, and third facets, having an LED mounted thereon and positioned to emit light energy upon respective ones of said portions of the tooth, and wherein each said LED is mounted on a heat sink, which is spaced from a corresponding respective outer surface of the first, second, and third facets, forming a heat insulation layer defined by an air gap between each said heat sink and the corresponding respective outer surface of the first, second, and third facets; and
- a control box electrically connected to the LEDs that controls the operation of the LEDs, capable of controlling power, curing mode, and light emitting selections.

10. The curing light of claim 9, wherein said second and third facets are oriented parallel to one another.

11. The curing light of claim 9, wherein said first facet is oriented at about ninety degree angle with respect to at least one of the second and third facets.

\* \* \* \* \*